United States Patent
Jung et al.

(10) Patent No.: US 10,208,328 B2
(45) Date of Patent: Feb. 19, 2019

(54) RAPID ANTIMICROBIAL SUSCEPTIBILITY TEST, BASED ON AN ANALYSIS OF CHANGES IN MORPHOLOGY AND GROWTH PATTERN OF A MICROBIAL CELL UNDER DIFFERENT CONCENTRATIONS OF VARIOUS ANTIMICROBIAL AGENTS, AND AUTOMATED CELL IMAGE ANALYSIS SYSTEM THEREFOR

(71) Applicant: Quanta Matrix Co., Ltd., Seoul (KR)

(72) Inventors: Yong-Gyun Jung, Seoul (KR); Eun-Geun Kim, Gyeonggi-do (KR); Jung Heon Yoo, Gyeonggi-do (KR); Sunghoon Kwon, Seoul (KR); Jungil Choi, Seoul (KR); Hee Chan Kim, Seoul (KR); Jung Chan Lee, Seoul (KR); Eui Jong Kim, Seoul (KR); Sang Hoon Song, Seoul (KR); Sei Ick Joo, Seoul (KR); Ji Soo Lee, Gyeonggi-do (KR)

(73) Assignee: QUANTAMATRIX INC., Seoul (KR)

( * ) Notice: Subject to any disclaimer, the term of this patent is extended or adjusted under 35 U.S.C. 154(b) by 235 days.

(21) Appl. No.: 14/883,101

(22) Filed: Oct. 14, 2015

(65) Prior Publication Data
US 2016/0102334 A1    Apr. 14, 2016

Related U.S. Application Data

(60) Provisional application No. 62/067,409, filed on Oct. 22, 2014.

(30) Foreign Application Priority Data

Oct. 14, 2014    (KR) .......................... 10-2014-0138535

(51) Int. Cl.
*C12Q 1/18*    (2006.01)

(52) U.S. Cl.
CPC ...... *C12Q 1/18* (2013.01); *G06T 2207/30024* (2013.01)

(58) Field of Classification Search
None
See application file for complete search history.

(56) References Cited

U.S. PATENT DOCUMENTS 7,615,373 B2 *    11/2009    Simpson ................... A61F 2/08
435/398

OTHER PUBLICATIONS

Aldrige et al. "Asymmetry and Aging of Mycobacterial Cells Lead to Variable Growth and Antibiotic Susceptibility" Science vol. 335, Jan. 6, 2012, 6pgs. Published online Dec. 15, 2011; (Year: 2011).*
Ingham et al. "Rapid antibiotic sensitivity testing and trimethoprim-mediated filamentation of clinical isolates of the Enterobacteriaceae assayed on a novel porous culture support" Journal of Medical Microbiology (2006), 55, 1511-1519 (Year: 2006).*
Lu et al. "Single Cell Antimicrobial Susceptibility Testing by Confined Microchannels and Electrokinetic Loading" Anal. Chem. 2013, 85, 3971-3976, published Feb. 27, 2013. (Year: 2013).*
Yao et al. "Distinct Single-Cell Morphological Dynamics under Beta-Lactam Antibiotics" Molecular Cell 48, 705-712, Dec. 14, 2012 (Year: 2012).*
Fredborg et al. "Real-Time Optical Antimicrobial Susceptibility Testing" J. Clin. Microbiol, 26 pgs. published online Apr. 17, 2013. (Year: 2013).*
Hou et al, Time lapse investigation of antibiotic susceptibility using a microfluidic linear gradient 3D culture device, Lab Chip, 2014, 14, 3409.
Jungil Choi, "Rapid and High Throughput Antimicrobial Susceptibility Test Using Morphological Analysis of Single Cells with Microfluidic Channel in 96 Well Platform," 17th International Conference on Minaturized Systems for Chemistry and Life Sciences; Oct. 27-31, 2013, Freiberg, Germany.
Jungil Choi, "Rapid and High Throughput Antimicrobial Susceptibility Test Using Morphological Analysis of Single Cells with Microfluidic Channel in 96 Well Platform," Poster Presentation of 2013 Fall Conference by The Korean BioChip Society; Nov. 13, 2013.

* cited by examiner

*Primary Examiner* — Thane Underdahl
(74) *Attorney, Agent, or Firm* — STIP Law Group, LLC

(57) ABSTRACT

Provided are a rapid antimicrobial susceptibility test, based on an analysis of changes in morphology and growth pattern of a microbial cell under different concentrations of various antimicrobial agents, and an automated cell image analysis system therefor. The antimicrobial susceptibility test is rapidly performed based on an analysis of changes in morphology and growth pattern of a microbial cell under different concentrations of various antimicrobial agents, and this makes it possible to obtain highly reliable test results faster by six to seven times than the standard method recommended by Clinical and Laboratory Standards Institute (CLSI).

6 Claims, 11 Drawing Sheets

Fig. 6

| Time Laps Images | | | Morphological Pattern | Numerical Interpretation of Morphology | Susceptibility Determination | Cases |
|---|---|---|---|---|---|---|
| 0 hr | 1.5 hrs (*2 hrs) | 3 hrs (*4 hrs) | | | | |
| A) *S. aureus* with penicillin | | | Dividing | | Resistant (Under MIC) | General Antimicrobials against all four standard strains |
| B) *E. faecalis* with vancomycin | | | No change | | | General Antimicrobials against *S. aureus* and *E. faecalis* and Non β-lactams against *P. aeruginosa* and *E. coli* |
| C) *P. aeruginosa* with aztreonam | | | Filamentary formation | | Susceptible MIC or Over MIC | β-lactams drug except penem class against *P. aeruginosa* and *E. coli* |
| D) *E. coli* with imipenem | | | Swelling formation | | | Penem class drug in β-lactams against *P. aeruginosa* and *E. coli* |

RAPID ANTIMICROBIAL SUSCEPTIBILITY TEST, BASED ON AN ANALYSIS OF CHANGES IN MORPHOLOGY AND GROWTH PATTERN OF A MICROBIAL CELL UNDER DIFFERENT CONCENTRATIONS OF VARIOUS ANTIMICROBIAL AGENTS, AND AUTOMATED CELL IMAGE ANALYSIS SYSTEM THEREFOR

CROSS-REFERENCE TO RELATED APPLICATIONS

This U.S. non-provisional patent application claims priority under 35 U.S.C. § 119 to Korean Patent Application No. 10-2014-0138535, filed on Oct. 14, 2014, and U.S. Provisional Patent Application No. 62/067,409, filed on Oct. 22, 2014, the entire contents of which are hereby incorporated by reference.

BACKGROUND OF THE INVENTION

Example embodiments of the inventive concept relate to a rapid antimicrobial susceptibility test, based on an analysis of changes in morphology and growth pattern of a microbial cell under different concentrations of various antimicrobial agents, and an automated cell image analysis system therefor. In particular, the antimicrobial susceptibility test is rapidly performed based on an analysis of changes in morphology and growth pattern of a microbial cell under different concentrations of various antimicrobial agents, and this makes it possible to obtain highly reliable test results faster by six to seven times than the standard method recommended by Clinical and Laboratory Standards Institute (CLSI).

An antimicrobial susceptibility test (AST) may be performed to estimate effects of antimicrobial agents that will be used for treatment of infectious diseases, and it may include examining whether there is susceptibility, based on a minimal inhibitory concentration (MIC).

A conventional method of testing a cell reaction to different drugs may include steps of disposing a cell in a liquid or solid medium, mixing a to-be-tested drug with the liquid medium (or disposing a paper disk, in which the drug is absorbed, on the solid medium) to react the drug with the cell, and measuring turbidity or absorbance representing an extent of a growth reaction of the cell to the drug. However, the conventional method is a statistical method of collecting information on many cells, not on a change of each cell, and thus, in order to obtain meaningful statistical results, the number of cells should be increased up to a specific value (typically, ten million per 1 ml or higher), and thus, it takes a long time to culture cells (typically, 16-24 hours). Furthermore, according to the conventional method, it is impossible to realize an observation of a change of each individual cell under a drug and an real-time observation of each motile cell real-time, and moreover, it takes a long time and great effort to test many drugs, because each drug should be injected by an individual injection process.

Furthermore, in the case where a solid medium is used for the AST method, a KB-test has a limitation on the number of samples that can be disposed on each medium plate, and thus, in order to perform an AST process for tens of different antimicrobial agents, many agar medium plates are required. Even when an automated system (e.g., VITEK system) capable of minimizing a test time is used for the AST process, a turbidity of bacteria should be increased up to a specific value, and thus, the AST process also suffers from a long test time (typically, 12 hours or more). In addition, since a test environment for the conventional method is different from a human body, the results may be largely different from the real phenomenon in the human body (Gregory G. Anderson, et al. (2003), "Intracellular Bacterial Biofilm-Like Pods in Urinary Tract Infections", Science 301, 105; Gallo et al. (2011), "Demonstration of *Bacillus cereus* in Orthopaedic-Implant-Related Infection with Use of a Multi-Primer Polymerase Chain Reaction-Mass Spectrometric Assay", J Bone Joint Surg Am, 93).

To overcome technical limitations of the conventional AST method, there have been proposed various methods, called rapid AST (RAST), which make it possible to observe the division of microbes at an initial step. For example, each of such known methods may include a step of measuring the number of microbial cells in micro-fluidic channel, measuring a rotation speed of a magnetic bead to estimate a weight of microbes, measuring a fluorescence signal associated with metabolic activity of microbial cells in liquid droplet, or calculating an area of an image, which is occupied by microbes, to estimate susceptibility to an antimicrobial agent.

Meanwhile, microbial reactions to antimicrobial agents are very heterogeneous and are specifically dependent on antimicrobial agent conditions, but the known methods are performed based on the observation for examining whether a microbe is growing. In other words, in the known methods, only the presence or absence of 'growth' of a microbial cell is observed, without consideration for various morphological changes (other than 'growth' or 'no-growth') of a microbial cell, which may occur under different conditions of antimicrobial agents, and thus, the known methods suffer from low reliability of AST results.

SUMMARY

To overcome these difficulties, the inventors have examined correlation between the changes in morphology and growth pattern of a microbial cell under different concentrations of various antimicrobial agents and the results of Broth Micro-dilution (BMD) experiment and have invented an accurate and rapid antimicrobial susceptibility test (AST) method based on the examination of the correlation. Here, the changes in morphology and growth pattern of a microbial cell under different concentrations of various antimicrobial agents are analyzed in the invented AST method, and in this sense, the invented AST method is different from the conventional method, in which only the presence or absence of the growth of a microbe is measured to determine antimicrobial susceptibility of the microbe to antimicrobial agents.

According to some aspects of the inventive concept, example embodiments of the inventive concept relate to an antimicrobial susceptibility (AST) method, based on an analysis of changes in morphology and growth pattern of a microbial cell under antimicrobial agents, and the AST method may include the steps of:

(a) reacting a microbe with an antimicrobial agent;
(b) imaging a change in morphology and growth pattern of a microbial cell over time;
(c) classifying the change in morphology and growth pattern of the microbial cell, based on the obtained image; and
(d) determining whether the microbe is resistant or susceptible to the antimicrobial agent, based on the classification on the change in morphology and growth pattern of the microbial cell.

In the AST method according to the inventive concept, the microbial cell may include a single microbial cell or a group of microbial cells.

In the AST method according to the inventive concept, in step (c), the change in morphology and growth pattern of the microbial cell may be classified into dividing, no-change, filament formation, and swelling formation.

In the AST method according to the inventive concept, in step (d), when the change in morphology and growth pattern of the microbial cell is classified as the dividing, the microbe may be determined to be resistant to the antimicrobial agent, and when the change in morphology and growth pattern of the microbial cell is classified as one of the no-change, the filament formation, and the swelling formation, the microbe may be determined to be susceptible to the antimicrobial agent.

In the AST method according to the inventive concept, the microbe may include *Enterococcus faecium, Staphylococcus aureus, Klebsiella species, Acinetobacter baumannii, Pseudomonas aeruginosa*, or *Enterobacter* species.

In the AST method according to the inventive concept, the filament formation may include a microbial reaction, except for a reaction of gram-negative bacteria including *Pseudomonas aeruginosa* and *Escherichia coli* to penems of β-lactam antimicrobial agents.

In the AST method according to the inventive concept, the swelling formation may include a microbial reaction of gram-negative bacteria including *Pseudomonas aeruginosa* and *Escherichia coli* to penems of β-lactam antimicrobial agents.

According to other aspects of the inventive concept, example embodiments of the inventive concept relate to an antimicrobial susceptibility (AST) method, which may be performed based on an analysis of changes in morphology and growth pattern of a microbial cell under antimicrobial agents. For example, the AST method may include the steps of:

(a) reacting a microbe with an antimicrobial agent;
(b) imaging a change in morphology and growth pattern of a microbial cell over time;
(c) inspecting an image obtained in step (b) to observe the change in morphology and growth pattern of the microbial cell; and
(d) determining an antimicrobial susceptibility of the microbe in such a way that, when the microbial cell is observed to be in a state of dividing, the microbial cell is determined to be resistant to the antimicrobial agent, and when the microbial cell is observed to be in a state of no-change, filament formation, or swelling formation, the microbial cell is determined to be susceptible to the antimicrobial agent.

According to still other aspects of the inventive concept, example embodiments of the inventive concept relate to an automated cell image analysis system configured to perform an antimicrobial susceptibility (AST) method, based on an analysis of changes in morphology and growth pattern of a microbial cell under antimicrobial agents, and the cell image analysis system may include:

(a) a culture chip for culture of a microbe and an antimicrobial agent and for an imaging of a change in morphology and growth pattern of a microbial cell;
(b) an optical image analysis device filming a culturing region of the microbial cell and detecting an image of the microbial cell; and
(c) a reader analyzing the detected image of the microbial cell to obtain information on a total area occupied by microbial cells, the number of microbial cells, and a total length of microbial cells and determining antimicrobial susceptibility of the microbial cell.

In the automated cell image analysis system for the AST method according to the inventive concept, the change in morphology and growth pattern of the microbe is classified into dividing, no-change, filament formation, and swelling formation, according to the total area occupied by microbial cells, the number of microbial cells, and the total length of microbial cells, and the antimicrobial susceptibility is determined based on the classification of the change in morphology and growth pattern of the microbe.

In the automated cell image analysis system for the AST method according to the inventive concept, the optical image analysis device may include a tungsten lamp, an LED device, or a laser light source, which serve as a visible light source for obtaining an optical image. The optical image analysis device may include a charge coupled device (CCD) or complementary metal oxide semiconductor (CMOS) camera for obtaining a cell image transmitted through an objective lens.

The use of the AST method according to the inventive concept (i.e., based on an analysis of changes in morphology and growth pattern of a microbial cell under antimicrobial agents) makes it possible to obtain a more accurate AST result, compared with that of the conventional AST method, as will be described with reference to the first embodiment. The use of the AST method according to the inventive concept (i.e., based on an analysis of changes in morphology and growth pattern of a microbial cell under antimicrobial agents) makes it possible to obtain accurately and rapidly obtain test results, compared with the AST method in accordance with CLSI guidelines, as will be described with reference to the second embodiment. The use of the AST method according to the inventive concept (i.e., based on an analysis of changes in morphology and growth pattern of a microbial cell under antimicrobial agents) makes it possible to accurately obtain the test results with a faster test time (by about 6-7 times), compared with the standard BMD method in accordance with CLSI guidelines, as will be described with reference to the fourth embodiment. In addition, the use of the AST method according to the inventive concept (i.e., based on an analysis of changes in morphology and growth pattern of a microbial cell under antimicrobial agents) makes it possible to obtain accurate results, even when a microbial cell is grown to exhibit a filament formation and swelling formation, as will be described with reference to the fifth embodiment.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

FIG. 1(A) is an image showing a structure of the MAC chip, and FIG. 1(B) shows a cell culturing region.

A) Normal growth (Amikacin): at a concentration lower than MIC, a bacterial cell was divided into two cells. However, at a concentration higher than MIC of Amikacin, there was substantially no division of a bacterial cell.

B) Filament formation (Piperacillin): at a concentration lower than MIC, a bacterial cell was divided into two cells. At a concentration higher than MIC, there was a formation of a filament (or longitudinal cell expansion) but there was no division of a bacterial cell. In some cases, not only the filament formation but also the cell division was found, and these cases were determined to be resistant.

C) Cell expansion (Imipenem): at a concentration lower than MIC, a bacterial cell was divided into two cells. At a concentration higher than MIC, a cell was expanded, but there was no division of a bacterial cell. In some cases, not only the swelling formation and the cell division were found, and these cases were determined to be resistant.

Figure 3:
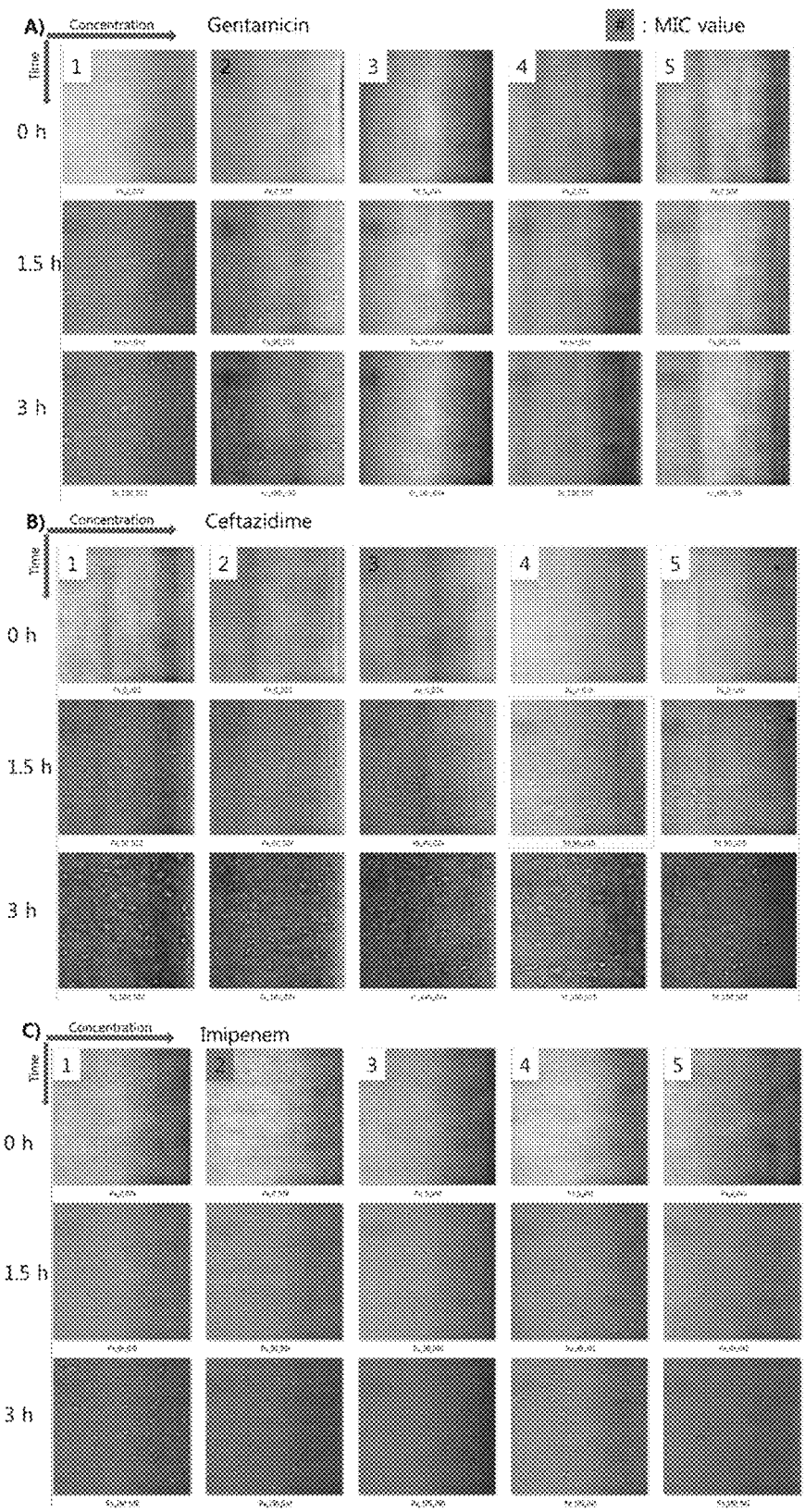

FIG. 3 shows MIC characteristics of P. aeruginosa ATCC 27853 to antimicrobial agents, according to example embodiments of the inventive concept.

A) Normal growth (Gentamicin): at a concentration lower than MIC, a bacterial cell was divided into two cells. However, at a concentration higher than MIC, there was substantially no division of a bacterial cell.

B) Filament formation (Ceftazidime): at a concentration lower than MIC, a bacterial cell was divided into two cells. At a concentration higher than MIC, a filament was formed, but there was no division of a bacterial cell. In some cases, not only the filament formation but also the cell division was found, and these cases were determined to be resistant.

C) Cell expansion (Imipenem): at a concentration lower than MIC, a bacterial cell was divided into two cells. However, at a concentration higher than MIC, there was an expansion of a bacterial cell. In some cases, not only the cell expansion and the cell division were found, and these cases were determined to be resistant.

Figure 4:
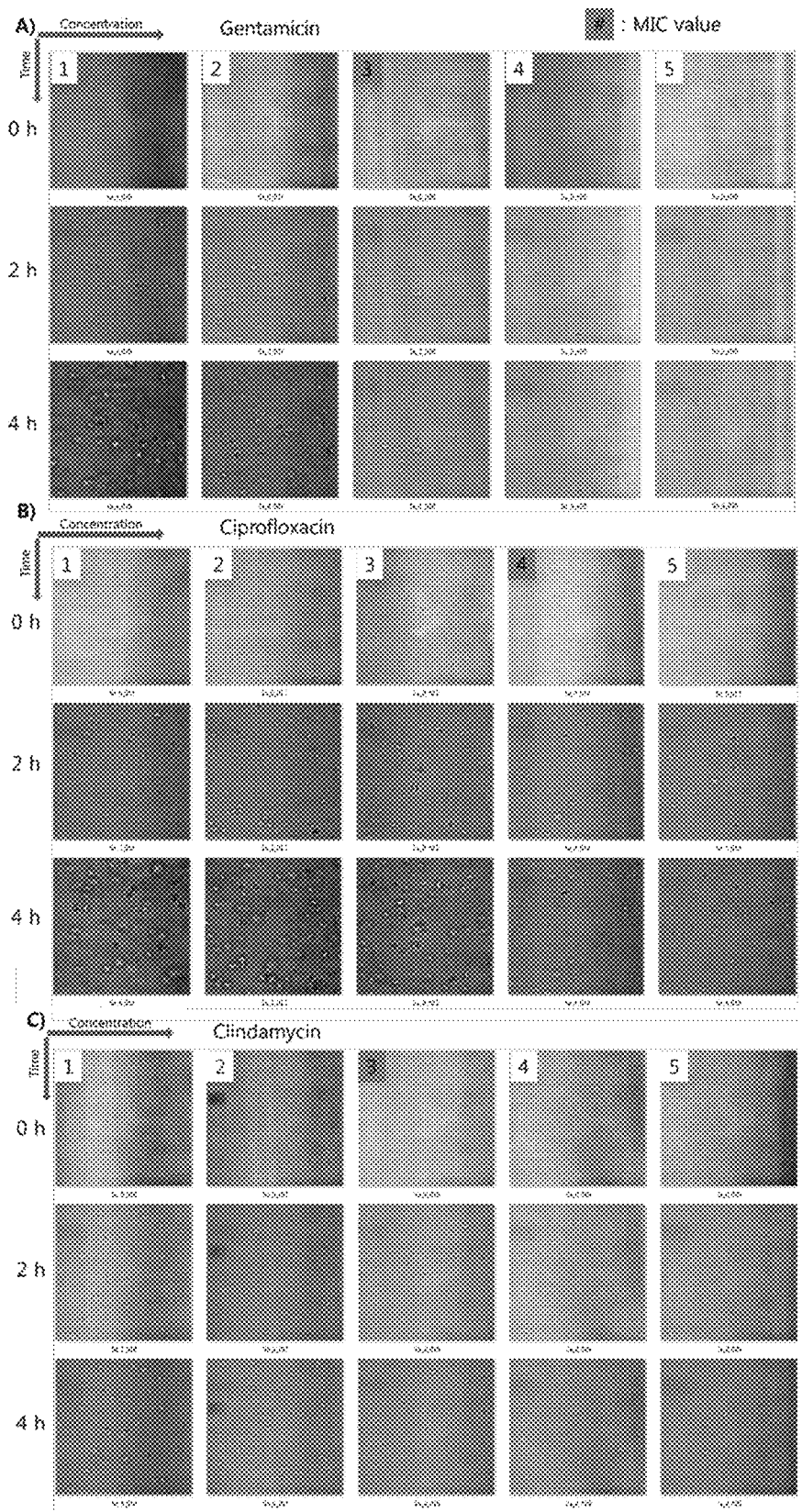

FIG. 4 shows MIC characteristics of S. aureus ATCC 29213 to antimicrobial agents, according to example embodiments of the inventive concept.

A) Normal growth (Gentamicin): at a concentration lower than MIC, a bacterial cell was divided into two cells, and thus, the total number of bacterial cells was increased. However, at a concentration higher than MIC, each of bacterial cells was scarcely divided into two cells.

B) Relatively rapid growth (RRG) (Ciprofloxacin): in the case of Ciprofloxacin, a bacterial cell was rapidly grown, and even at a concentration of MIC or higher, a bacterial cell was rapidly divided into two cells for two hours. However, after four hours, there was no more division of a bacterial cell. It was found that there was a meaningful difference in growth speed between concentrations higher and lower than MIC. The MIC value was determined based on relative growth of a cell.

C) Relatively slow growth (RSG) (Clindamycin): in the case of clindamycin, although, even at a concentration lower than MIC, a bacterial cell was very slowly divided, there was a meaningful difference in growth speed between concentrations higher and lower than MIC. The MIC value was determined by a relative cell growth.

Figure 5:
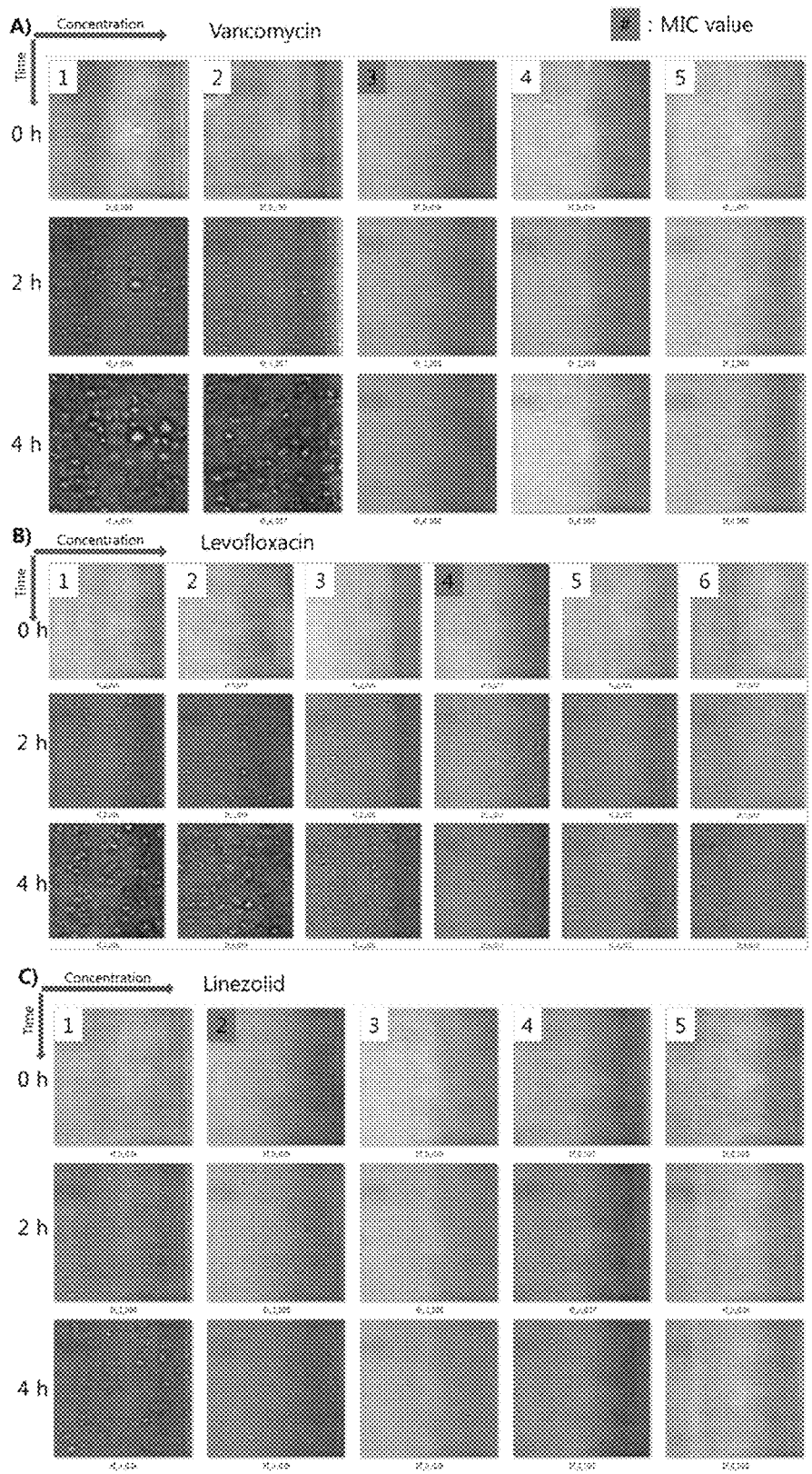

FIG. 5 shows MIC characteristics of E. faecalis ATCC 29212 to antimicrobial agents, according to example embodiments of the inventive concept.

A) Normal growth (Vancomycin): at a concentration lower than MIC, each of bacterial cells was divided into two cells, and thus, the total number of the bacterial cells was increased. However, at a concentration higher than MIC, each single bacteria cell was scarcely divided into two cells.

B) Relatively rapid growth (RRG) (levofloxacin): in the case of levofloacin, even at a concentration of MIC or higher, each of bacterial cells was divided into two cells within two hours, but after four hours, there was no more division of a bacterial cell. It was found that there was a meaningful difference in growth speed between concentrations higher and lower than MIC.

C) Relatively slow growth (RSG) (linezolid): in the case of linezolid, although, even at a concentration lower than MIC, a bacterial cell was very slowly divided, there was a meaningful difference in growth speed between concentrations higher and lower than MIC. The MIC value was determined based on relative growth of a cell under different concentrations of antimicrobial agents.

FIG. 6 shows results of an antimicrobial susceptibility analysis, according to a first embodiment of the inventive concept. (* Images of gram-positive bacterias were taken at times of 0, 2, and 4 hour. The bar represents 20 pm.)

Figure 7:
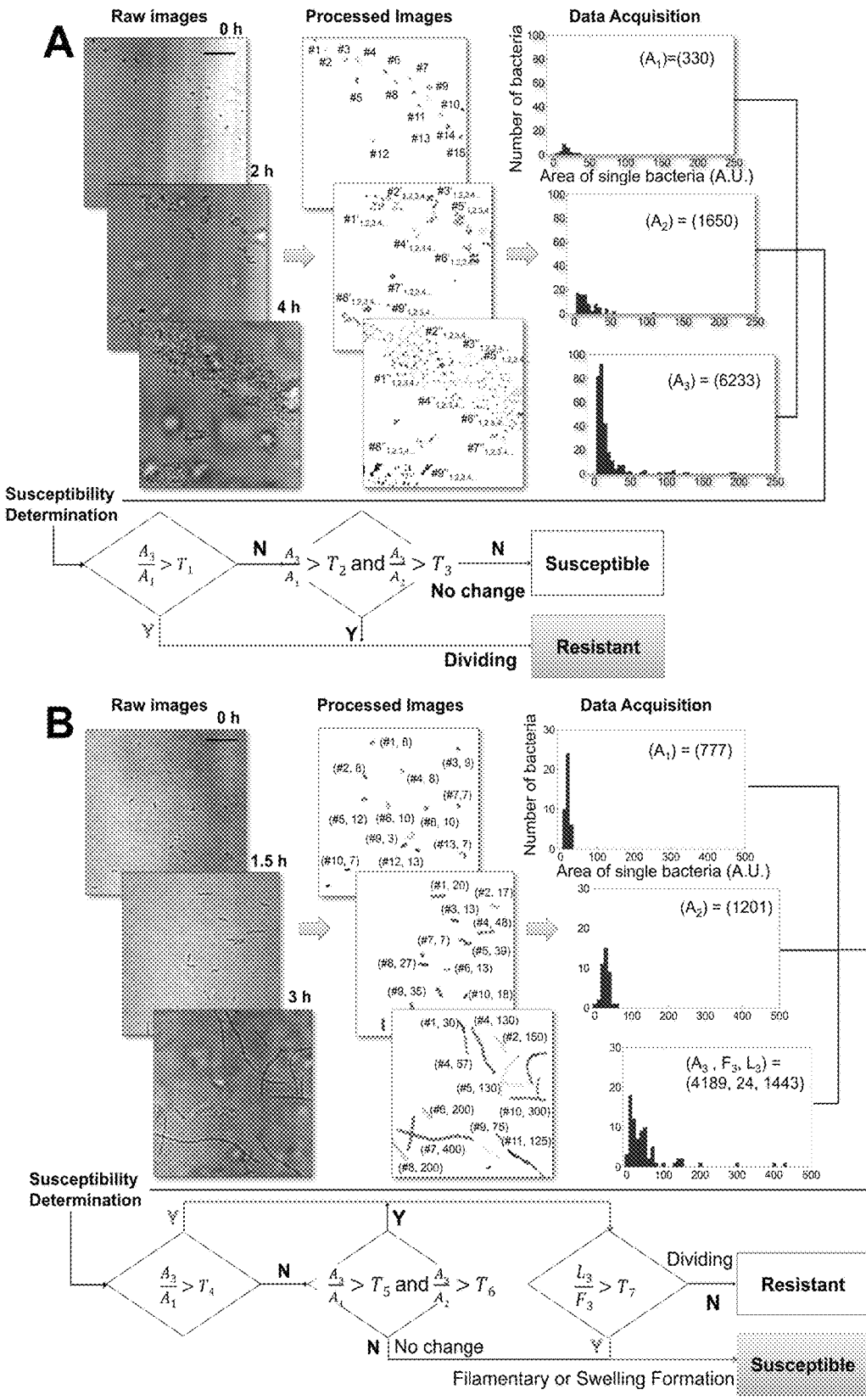

FIG. 7 is a schematic diagram exemplarily illustrating an image detection method and an antimicrobial susceptibility test method, which are performed using an automated cell image analysis system, according to example embodiments of the inventive concept.

Figure 8:
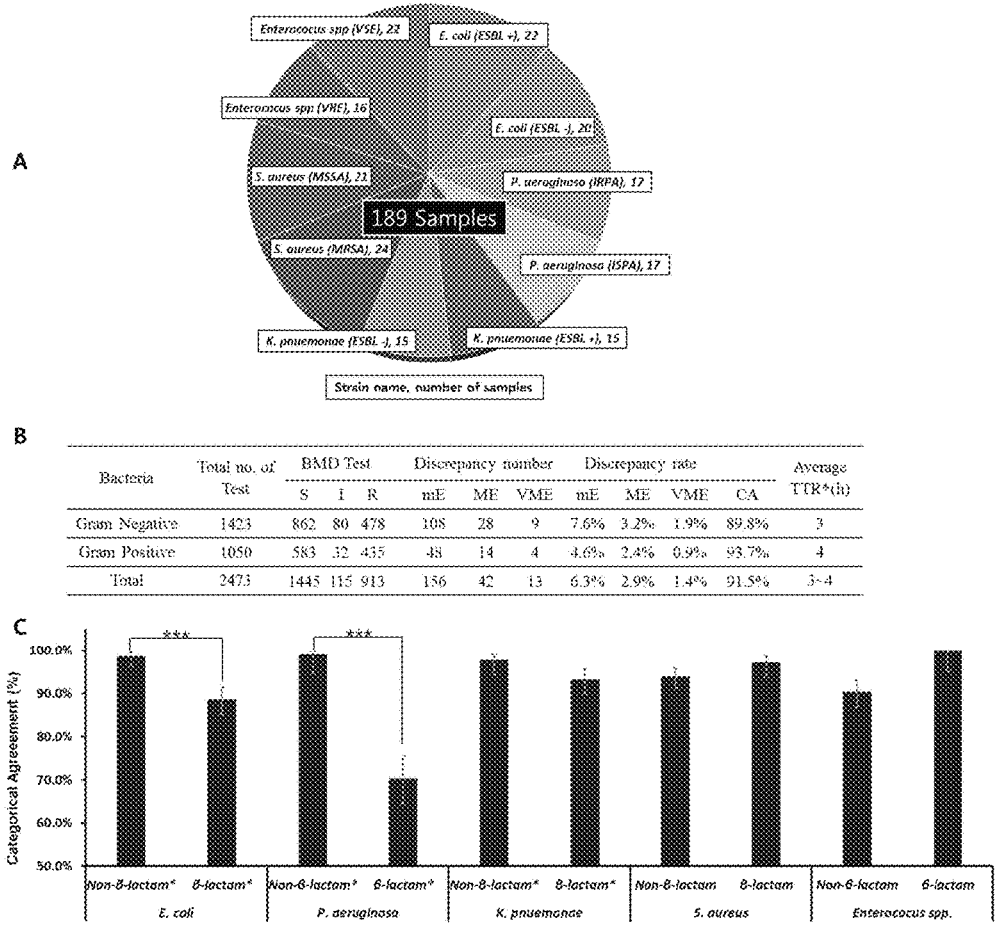

FIG. 8 shows comparison of MIC characteristics between the AST method according to a fourth embodiment of the inventive concept and the standard method. FIG. 8(A) represents an object strain used for the fourth embodiment of the inventive concept. FIG. 8(B) is a table showing discrepancy rates (DR) and categorical agreement (CA) rates. FIG. 8(C) represents CA rates of clinical strains to β-lactam and non-β-lactam based antimicrobial agents (***P<0.001).

*S: susceptibility; I: intermediate susceptibility; R: resistance; mE: minor error (it is determined as R or S for the standard BMD method and as I for example embodiments of the inventive concept; Or, it is determined as I for the standard BMD method and as R or S for example embodiments of the inventive concept); ME: major error (it is determined as S for the standard BMD method and as R for example embodiments of the inventive concept); VME: very major error (it is determined as R for the standard BMD method and as S for example embodiments of the inventive concept); TTR: the time taken to obtain the measurement.

Figure 9:
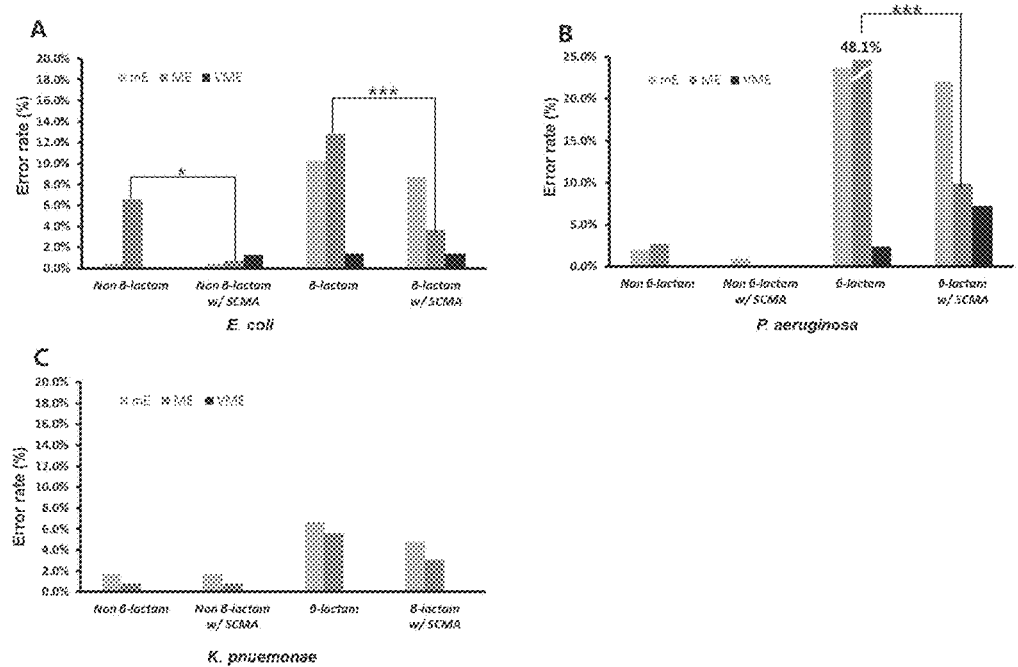

FIG. 9 shows a reduction of error rate achieved by a method according to a fifth embodiment of the inventive concept, when there are filament and swelling formations (*P<0.05 and ***P<0.001).

Figure 10:
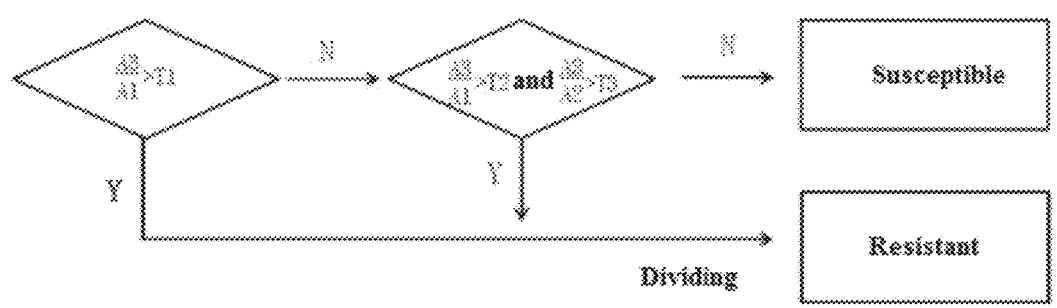

FIG. 10 is a diagram to determine whether the microbial cell has antimicrobial susceptibility.

Figure 11:
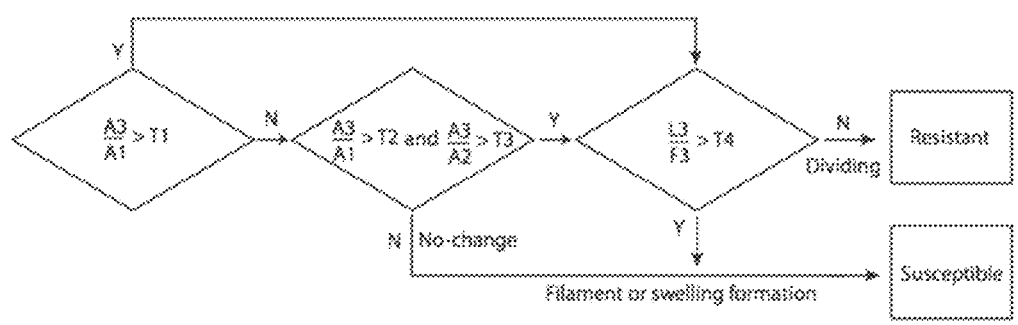

FIG. 11 is a diagram to determine whether the microbial cell has antimicrobial susceptibility.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Unless defined otherwise, all technical and scientific terms used herein have the same meaning as commonly understood by one of ordinary skill in the art to which the disclosure pertains. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. Although any methods and materials similar or equivalent to those described herein can be used in the practice for testing of the disclosure(s), specific examples of appropriate materials and methods are described herein. The inventive concept can be variously used depending on the context thereof, and thus, it should not be construed to be limited to a specific one of methods, protocols, and reagents.

As used in the present specification, the singular forms "a", "an", and "the" include plural references unless the context clearly dictates otherwise. As used in the present specification, the term "or" may have the same meaning as 'and/or', unless the context clearly dictates otherwise. It is to be understood that the terms "including", "comprising", "consisting" and grammatical variants thereof do not preclude the addition of one or more components, features, steps, integers or groups thereof and that the terms are not to be construed as specifying components, features, steps or integers.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. All documents cited are, in relevant part, incorporated herein by reference; the citation of any document is not to be construed as an admission that it is prior art with respect to the present invention.

The title of the present specification is provided to express one or more aspects of the inventive concept, but it is not intended to suggest any limitation to the scope of the inventive concept.

Example embodiments of the inventive concept provide antimicrobial susceptibility (AST) methods, which are performed based on an analysis of changes in morphology and growth pattern of a microbial cell under different concentrations of various antimicrobial agents, and an automated cell image analysis system therefor.

According to example embodiments of the inventive concept, an antimicrobial susceptibility (AST) method may be performed based on an analysis of changes in morphology and growth pattern of a microbial cell under antimicrobial agents. For example, the AST method may include the steps of:
(a) reacting a microbe with an antimicrobial agent;
(b) imaging a change in morphology and growth pattern of a microbial cell over time;
(c) classifying the change in morphology and growth pattern of a microbial cell, based on an obtained image; and
(d) determining resistance and susceptibility of the microbe to the antimicrobial agent, based on the classification of the change in morphology and growth pattern of a microbial cell.

In the AST method according to the inventive concept, in step (c), the change in morphology and growth pattern of the microbial cell may be classified into dividing, no-change, filament formation, and swelling formation.

In the AST method according to the inventive concept, in step (d), when the change in morphology and growth pattern of a microbial cell is classified as the dividing, the microbe may be determined to be resistant to the antimicrobial agent, and when the change in morphology and growth pattern of a microbial cell is classified as one of the no-change, the filament formation, and the swelling formation, the microbe may be determined to be susceptible to the antimicrobial agent.

In the present specification, the term "microbe" may refer to all of gram-negative (Gram −) and gram-positive (Gram+) bacteria, Eumycetes, Archimycetes, and so forth, but example embodiments of the inventive concept are not limited thereto. In detail, the microbe may be at least one selected from the group consisting of *Enterococcus, Streptococcus, Pseudomonas, Salmonella, Escherichia coli, Staphylococcus, Lactococcus, Lactobacillus, Enterobacteriacae, Klebsiella, Providencia, Proteus, Morganella, Acinetobacter, Burkholderia, Stenotrophomonas, Alcaligenes,* and *Mycobacterium*, but example embodiments of the inventive concept are not limited thereto. In more detail, the microbe may include *Enterococcus faecium, Staphylococcus aureus, Klebsiella* species, *Acinetobacter baumannii, Pseudomonas aeruginosa,* and *Enterobacter* species, but example embodiments of the inventive concept are not limited thereto.

In the present specification, the term "antimicrobial agents" may refer to at least one selected from the group consisting of Amikacin, Amoxicillin, Ampicillin, Aztreonam, Benzylpenicillin, Clavulanic Acid, Cefazolin, Cefepime, Cefotaxime, Cefotetan, Cefoxitin, Cefpodoxime, Ceftazidime, Ceftriaxone, Cefuroxime, Ciprofloxacin, Dalfopristin, Doripenem, Daptomycin, Ertapenem, Erythromycin, Gentamicin, Imipenem, Levofloxacin, Linezolid, Meropenem, Minocycline, Moxifloxacin, Nitrofurantoin, Norfloxacin, Piperacillin, Quinupristin, Rifampicin, Streptomycin, Sulbactam, Sulfamethoxazole, Telithromycin, Tetracycline, Ticarcillin, Tigecycline, Tobramycin, Trimethoprim, and Vancomycin, but example embodiments of the inventive concept are not limited thereto.

In the present specification, the expression "changes in morphology and growth pattern of a microbial cell" may refer to a reaction of a microbial cell to an antimicrobial agent, and such changes of a microbial cell may be classified into dividing, no-change, filament formation, and swelling formation. Here, the expression "changes in morphology and growth pattern of a microbial cell" may be interchangeably used with an expression "morphological change of a microbial cell".

The term "dividing" may mean that a microbial cell is divided into two cells under non-antibiotic and antibiotic resistant conditions, and consequently, that not only the number of microbial cells but also an OD value of BMD experiment are increased.

The term "no-change" may mean that a microbial cell is susceptible to an antimicrobial agent and is not growing.

The term "filament formation" may mean that a microbial cell is not dividing but is growing in its length direction. The filament formation may include a microbial reaction to β-lactam antimicrobial agents. In detail, the filament formation may include a microbial reaction, except for a reaction of gram-negative bacteria to some (e.g., penems) of β-lactam antimicrobial agents. In more detail, the filament formation may include a microbial reaction, except for a reaction of *Pseudomonas aeruginosa* or *Escherichia coli* to some (e.g., penems) of β-lactam antimicrobial agents.

The term "swelling formation" may mean that a microbial cell is not dividing but is swelling and growing. The swelling formation may include a microbial reaction to some (e.g., penems) of β-lactam antimicrobial agents. For example, the swelling formation may include a reaction of gram-negative bacteria to imipenem or meropenem. In detail, the swelling formation may include reactions of *Pseudomonas aeruginosa* and *Escherichia coli* to imipenem or meropenem.

The change in morphology and growth pattern of a microbial cell may be observed by imaging a single microbial cell or a group of microbial cells over time.

Accordingly, the AST method according to the inventive concept is be performed based on an analysis of changes in morphology and growth pattern of a microbial cell under antimicrobial agents, and this makes it possible to prevent a microbial cell from dividing. Accordingly, even when an OD value of BMD experiment is constant, it is possible to precisely and rapidly determine the presence or absence of an antimicrobial susceptibility.

According to other example embodiments of the inventive concept, an AST method may be performed based on an analysis of changes in morphology and growth pattern of a microbial cell under antimicrobial agents. For example. The AST method may include the steps of:
(a) reacting a microbe with an antimicrobial agent;
(b) imaging a change in morphology and growth pattern of a microbial cell over time;
(c) inspecting an image obtained in step (b) to observe the change in morphology and growth pattern of a microbial cell; and
(d) determining an antimicrobial susceptibility of the microbe in such a way that, when the microbial cell is observed to be in a state of dividing, the microbial cell is determined to be resistant to the antimicrobial agent, and when the microbial cell is observed to be in a state of no-change, filament formation, or swelling formation, the microbial cell is determined to be susceptible to the antimicrobial agent.

According to still other example embodiments of the inventive concept, an automated cell image analysis system, which is configured to perform an antimicrobial susceptibility (AST) method, based on an analysis of changes in morphology and growth pattern of a microbial cell under antimicrobial agents, may be provided. For example, the cell image analysis system may include:
(a) a culture chip for culture of a microbe and an antimicrobial agent and for an imaging of a change in morphology and growth pattern of a microbial cell;
(b) an optical image analysis device filming a culturing region of the microbial cell and detecting an image of the microbial cell; and
(c) a reader analyzing the detected image of the microbial cell to obtain information on a total area occupied by microbial cells, the number of microbial cells, and a total length of microbial cells and determining antimicrobial susceptibility of the microbial cell.

In the automated cell image analysis system, which is configured to perform an antimicrobial susceptibility (AST), based on an analysis of changes in morphology and growth pattern of a microbial cell under antimicrobial agents, according to the inventive concept, the antimicrobial susceptibility may be determined based on a change type (i.e., dividing, no-change, filament formation, and swelling formation) classified according to a total area occupied by microbial cells, the number of microbial cells, and a total length of microbial cells.

With regard to the term "culture chip" used in the present specification, although there is no specific limitation on the type of culture chip, MAC 2.0™ (Quanta Matrix) was used as the culture chip, in the following embodiments.

The term "optical image analysis device" used in the present specification may refer to a device for filming a culturing region of a microbial cell and obtaining an image of the microbial cell and may include a tungsten lamp, an LED device, or a laser light source, which serve as a visible light source for obtaining an optical image. The optical image analysis device may include a charge coupled device (CCD) or complementary metal oxide semiconductor (CMOS) camera for obtaining a cell image transmitted through an objective lens.

The term "reader" used in the present specification may refer to a device for analyzing the obtained image of the microbial cell and determining whether the microbial cell has antimicrobial susceptibility and such operations of the reader may be performed based on a total area occupied by microbial cells, the number of microbial cells, and total length of microbial cells.

In detail, the reader may perform operations of dividing a value (A3) of a total area occupied by microbial cells in a final image (e.g., obtained after 4 hours) by a value (A1) of the total area in an initial image (i.e., at 0 hour), comparing it with a first threshold value (T1), and then
a) determining that the microbial cell is resistant, when A3/A1 is greater than T1, and
b) performing comparison with a second threshold value (T2) and a third threshold value (T3), when A3/A1 is smaller than T1, to determine that, i) if A3/A1 and A3/A2 are greater than each of T2 and T3, the microbial cell is resistant, and ii) otherwise, the microbial cell is susceptible (here, A2 is a total area occupied by microbial cells in an image obtained after 2 hours). These operations may be performed as illustrated in FIG. 10.

Furthermore, when the total area occupied by microbial cells is increased above threshold values T4, T5, and T6, the reader may perform an operation of dividing the total length (L) of microbial cells by the number (F) of microbial cells. Thereafter, when the value of L/F is greater than T7, the change is classified as a filament formation or a swelling formation and the microbial cell is determined to be susceptible, and otherwise, the microbial cell is determined to be resistant. (Here, the threshold values T1, T2, T3, T4, T5, T6, and T7 may be individually determined using different growth rates under conditions of various antimicrobial agents). These operations may be performed as illustrated in FIG. 11.

Thus, by using the automated cell image analysis system, which is configured to perform an antimicrobial susceptibility (AST) method using an analysis of changes in morphology and growth pattern of a microbial cell under antimicrobial agents, according to the inventive concept, it is possible to precisely and rapidly examine whether there is an antimicrobial susceptibility, using the total length (L) of microbial cells, even for the cases of filament formation or swelling formation, even when a cell is not dividing and there is no change in the number (F) of microbial cells.

Hereinafter, various embodiments will be exemplarily described to provide a better understanding of the inventive concept. Therefore, the scope of the present inventive concept should not be construed as being limited to the embodiments set forth herein.

EXAMPLE EMBODIMENTS

[First Embodiment] AST Based on an Analysis of Changes in Morphology and Growth Pattern of a Microbial Cell Under Antimicrobial Agents (1) Objective Strain Four reference strains (*E. coli* ATCC 25922, *S. aureus* ATCC 29213, *P. aeruginosa* ATCC 27853, and *E. faecalis* ATCC 29212) were used as objective strains, in accordance with Clinical and Laboratory Standards Institute (CLSI) guidelines.

(2) Objective Antimicrobial Agents

To compare antimicrobial susceptibility of *E. coli* ATCC 25922 and *S. aureus* ATCC 29213 with that of the standard method, Amikacin, Amoxicillin/Clavulanic Acid, Ampicillin, Aztreonam, Cefazolin, Cefepime, Cefotaxime, Cefoxitin, Ceftazidime, Ciprofloxacin, Gentamicin, Imipenem, Norfloxacin, Meropenem, Piperacillin, Piperacillin/Tazobactam, Tetracyclin, Trimethoprim/Sulfamethoxazole, Ticarcilin, Trcarcillin/Clavulanic acid and Tobramycin were used as objective antimicrobial agents, and for *P. aeruginosa* ATCC 27853 and *E. faecalis* ATCC 29212, Ampicillin, Amoxicillin/Clavulanic Acid, Ciprofloxacin, Clindamycin, Erythromycin, Gentamicin, Imipenem, Levofloxacin, Linezolid, Oxacillin, Norfloxacin, Penicillin, Rifampin, Streptomycin, Teicoplanin, Tetracycline, Trimethoprim/sulfamethoxazole and Vancomycin were included in the objective antimicrobial agents.

Figure 1:
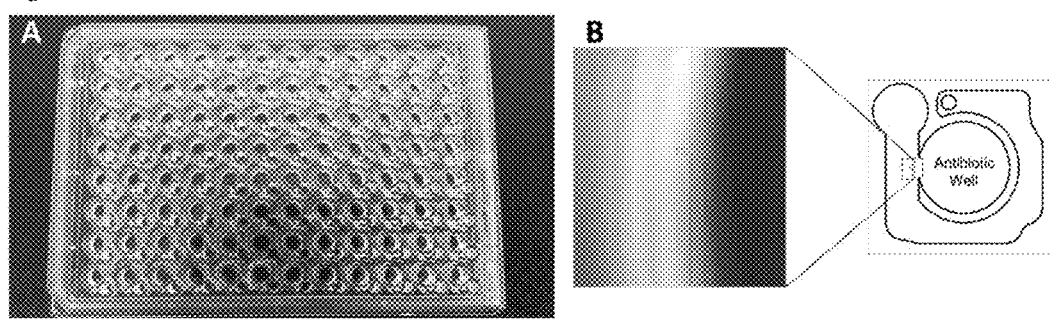
FIG. 1 illustrate MAC 2.0™ (Quanta Matrix) that was used in a first embodiment.
Figure 2:
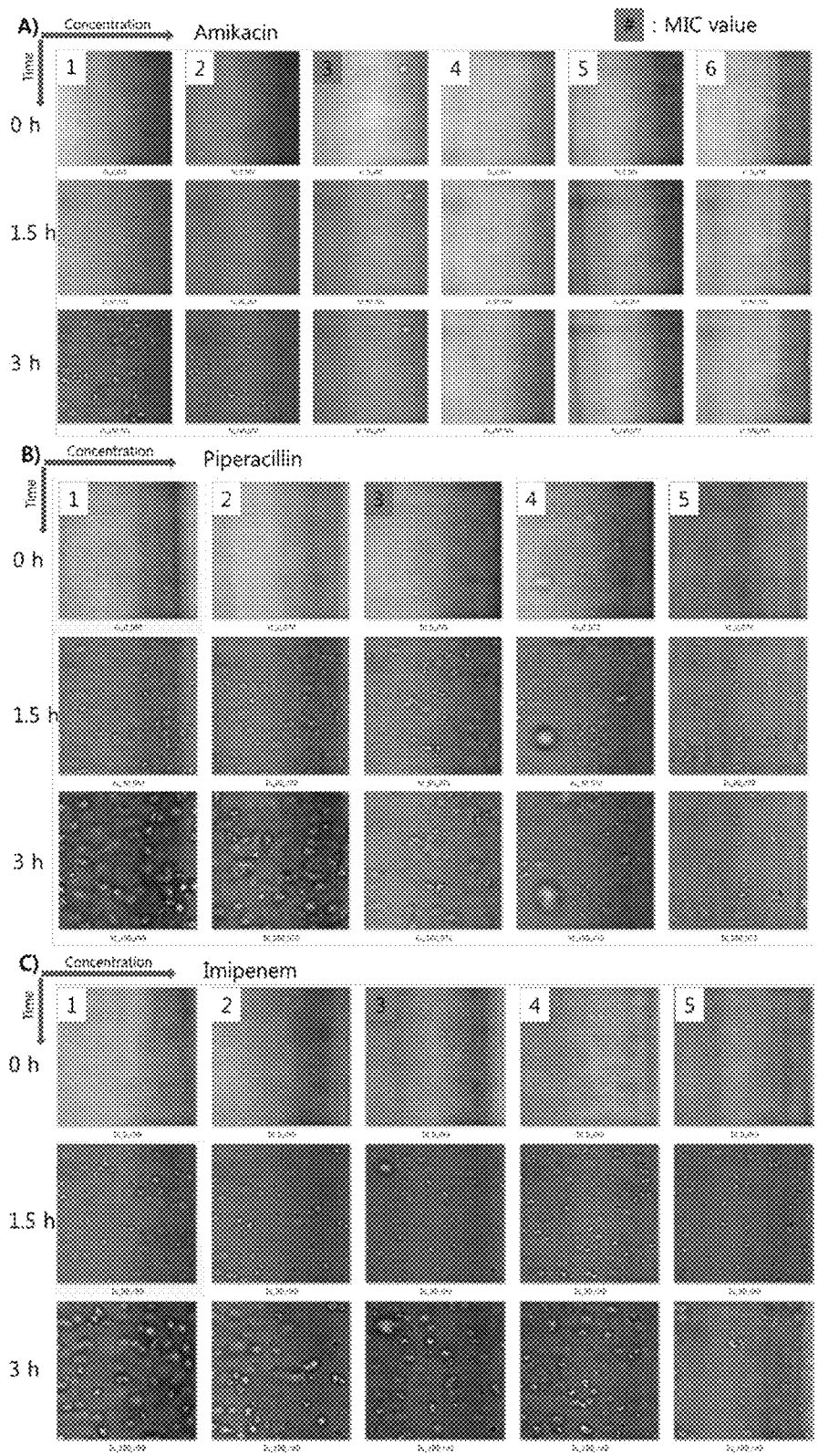
FIG. 2 shows MIC characteristics of *E. coli* ATCC 25922 to antimicrobial agents, according to example embodiments of the inventive concept.

(3) AST based on an analysis of changes in morphology and growth pattern of a microbial cell MAC 2.0™ (QuantaMatrix) of FIG. 1 was used to immobilize four objective strains, which were prepared to have the standard turbidity, on an agarose well and to inject antimicrobial agents (with a volume of 100 µl and appropriate concentration) into an antimicrobial agent well. The bacterial cell in MAC 2.0™ (QuantaMatrix) was monitored through a S Plan Fluor ELWD 60× (NA 1.49) lens of an inverted optical microscope (Eclipse Ti—Nikon, IX71—Olympus) provided in a heating system, and then, an electron multiplying CCD camera (QuantEM:512SC Photometrics for Eclipse Ti) was used to obtain images of a region where is adjacent to an interface between the agarose well of MAC 2.0™ and the antimicrobial agents well, over time. FIGS. 2 through 5 show the results.

Changes in morphology and growth pattern of the four reference strains (i.e., *E. coli* ATCC 25922, *S. aureus* ATCC 29213, *P. aeruginosa* ATCC 27853, and *E. faecalis* ATCC 29212) according to the kind of antimicrobial agent can be summarized as follow:

TABLE 1

| *E. coli* ATCC 25922 | Criteria | Category | Antimicrobial Class |
|---|---|---|---|
| Amikacin | Normal | Non-β-lactams | aminoglycosides |
| Amoxicillin/Clavulanic Acid | Swelling | β-lactams | Penicillins/β-lactamase inhibitor |
| Ampicillin | Filament | β-lactams | penicillins |
| Aztreonam | Filament | β-lactams | monobactams |
| Cefazolin | Filament | β-lactams | cephems |
| Cefepime | Filament | β-lactams | cephems |
| Cefotaxime | Filament | β-lactams | cephems |

TABLE 1-continued

| *E. coli* ATCC 25922 | Criteria | Category | Antimicrobial Class |
|---|---|---|---|
| Cefoxitin | Filament | β-lactams | cephems |
| Ceftazidime | Filament | β-lactams | cephems |
| Ciprofloxacin | Normal | Non-β-lactams | fluoroquinolone |
| Gentamicin | Normal | Non-β-lactams | aminoglycosides |
| Imipenem | Swelling | β-lactams | penems |
| Norfloxacin | Normal | Non-β-lactams | quinolones |
| Piperacillin | Filament | β-lactams | penicillins |
| Piperacillin/Tazobactam | Filament | β-lactams | Penicillins/β-lactamase inhibitor |
| Tetracycline | Normal | Non-β-lactams | tetracyclines |
| Trimethoprim/Sulfamethoxazole | Normal | Non-β-lactams | folate pathway inhibitors |

TABLE 2

| *P. aeruginosa* ATCC 27853 | Criteria | Category | Antimicrobial Class |
|---|---|---|---|
| Amikacin | Normal | Non-β-lactams | aminoglycosides |
| Aztreonam | Filament | β-lactams | monobactams |
| Cefepime | Filament | β-lactams | cephems |
| Cefotaxime | Filament | β-lactams | cephems |
| Ceftazidime | Filament | β-lactams | cephems |
| Ciprofloxacin | Normal | Non-β-lactams | fluoroquinolone |
| Gentamicin | Normal | Non-β-lactams | aminoglycosides |
| Imipenem | Swelling | β-lactams | penems |
| Meropenem | Swelling | β-lactams | penems |
| Piperacillin | Filament | β-lactams | penicillins |
| Piperacillin/Tazobactam | Filament | β-lactams | Penicillins/β-lactamase inhibitor |
| Ticarcilin | Filament | β-lactams | penicillins |
| Ticarcillin/Clavulanic acid | Filament | β-lactams | Penicillins/β-lactamase inhibitor |
| tobramycin | Normal | Non-β-lactams | aminoglycosides |

TABLE 3

| *S. aureus* ATCC 29213 | Criteria | Category | Antimicrobial Class |
|---|---|---|---|
| Ampicillin | Normal | β-lactams | penicillins |
| Amoxicillin/Clavulanic Acid | Normal | β-lactams | Penicillins/β-lactamase inhibitor |
| Ciprofloxacin | RRG | Non-β-lactams | fluoroquinolone |
| Clindamycin | RSG | Non-β-lactams | lincosamides |
| erythromycin | RSG | Non-β-lactams | macrolides |
| Gentamicin | Normal | Non-β-lactams | aminoglycosides |
| Imipenem | Normal | β-tactams | penems |
| Levofloxacin | RRG | Non-β-lactams | quinolones |
| Linezolid | RSG | Non-β-lactams | oxazolidinones |
| Oxacillin | RRG | β-lactams | penicillins |
| Penicillin | Normal | β-lactams | penicillins |
| Rifampin | RSG | Non-β-lactams | ansamycins |
| Tetracycline | Normal | Non-β-lactams | tetracyclines |
| Trimethoprim/sulfamethoxazole | RRG | Non-β-lactams | folate pathway inhibitors |
| Vancomycin | Normal | Non-β-lactams | glycopeptides |

TABLE 4

| *E. faecalis* ATCC 29212 | Criteria | Category | Antimicrobial Class |
|---|---|---|---|
| Ampicillin | Normal | β-lactams | penicillins |
| Ciprofloxacin | RRG | Non-β-lactams | fluoroquinolone |
| erythromycin | RSG | Non-β-lactams | macrolides |
| Gentamicin High Level | Normal | Non-β-lactams | aminoglycosides |
| Levofloxacin | RRG | Non-β-lactams | quinolones |
| Linezolid | RSG | Non-β-lactams | oxazolidinones |
| Norfloxacin | RRG | Non-β-lactams | quinolones |

TABLE 4-continued

| E. faecalis ATCC 29212 | Criteria | Category | Antimicrobial Class |
|---|---|---|---|
| Penicillin | Normal | β-lactams | penicillins |
| Rifampin | RSG | Non-β-lactams | ansamycins |
| Streptomycin High Level | Normal | Non-β-lactams | aminoglycosides |
| Teicoplanin | Normal | Non-β-lactams | glycopeptides |
| Tetracycline | RSG | Non-β-lactams | tetracyclines |
| Vancomycin | Normal | Non-β-lactams | glycopeptides |

(4) Results

A summary of AST results obtained from changes in morphology and growth pattern of the objective strains is illustrated in FIG. 6. Referring to FIG. 6, when the antimicrobial susceptibility is determined by the standard AST method per CLSI guidelines, a sample illustrated in a portion (A) of FIG. 6 was determined to be resistance to the antimicrobial agents, because an OD value obtained by the BMD method was increased, whereas samples illustrated in portions B, C, and D of FIG. 6 were determined to be susceptible to the antimicrobial agents, because the OD values obtained by the BMD method were decreased. In the cases of portions C and D of FIG. 6, there was no dividing and cells were growing, but the samples were determined to be susceptible; that is, it was found that the standard AST method gives an inaccurate AST result.

By contrast, when the antimicrobial susceptibility is determined by the AST method according to the inventive concept (i.e., based on an analysis of changes in morphology and growth pattern of a microbial cell), the sample illustrated in the portion (A) of FIG. 6 was determined to be resistance to the antimicrobial agents, because the morphological pattern thereof was classified as a case of dividing, and the sample illustrated in the portion (B) of FIG. 6 was determined to be susceptible to the antimicrobial agents, because the morphological pattern thereof was classified as a case of no-change. The sample illustrated in the portion (C) of FIG. 6 was determined to be susceptible to the antimicrobial agents, because the morphological pattern thereof was classified as a case of filament formation, and the sample illustrated in the portion (D) of FIG. 6 was determined to be susceptible to the antimicrobial agents, because the morphological pattern thereof was classified as a case of swelling formation. That is, it was found that the AST method according to the inventive concept gives a more accurate AST result, compared with that of the conventional AST method.

[Second Embodiment] Evaluation on Accuracy and Rapidity of the AST Method According to the Inventive Concept In the AST method according to the inventive concept, minimal inhibitory concentration (MIC) was measured using the changes in morphology and growth pattern of the four reference strains (i.e., E. coli ATCC 25922, S. aureus ATCC 29213, P. aeruginosa ATCC 27853, and E. faecalis ATCC 29212) and was compared with MIC quality control (QC) per CLSI guidelines. The following table 5 shows the results.

TABLE 5

Comparison of MIC values according to proposed method and QC of CLSI

Gram Negative Strains

| | E. coli ATCC 25922 | | P. aeruginosa ATCC 27853 | |
|---|---|---|---|---|
| Antimicrobial | SCMA Results | CLSI QC range | SCMA Results | CLSI QC range |
| Amikacin | 0.5~1 | 0.5~4 | 1~2 | 1~4 |
| Amoxicillin/ Clavulanic acid | 4/2 | 2/1~8/4 | — | — |
| Ampicillin | 2~4 | 2~8 | — | — |
| Aztreonam | 0.12 | 0.06~0.25 | 2~4 | 2~8 |
| Cefazolin | 2 | 1~4 | — | — |
| Cefepime | 0.03~0.06 | 0.015~0.12 | 0.5~2 | 0.5~4 |
| Cefotaxime | 0.06 | 0.03~0.12 | 16 | 8~32 |
| Cefoxitin | 2 | 2~8 | — | — |
| Ceflazidime | 0.5 | 0.06~0.5 | 2~4 | 1~4 |
| Ciprofloxacin | 0.004~0.008 | 0.004~0.015 | 0.25~0.5 | 0.25~1 |
| Gentamicin | 0.25 | 0.25~1 | 0.5~1 | 0.5~2 |
| Imipenem | 0.12 | 0.06~0.25 | 1 | 1~4 |
| Norfloxacin | 0.03~0.06 | 0.03~0.12 | — | — |
| Meropenem | — | — | 1 | 0.25~1 |
| Piperacillin | 2 | 1~4 | 4~8 | 1~8 |
| Piperacillin/ Tazobactam | 1/4~2/4 | 1/4~4/4 | 2/4~8/4 | 1/4~8/4 |
| Tetracycline | 1 | 0.5~2 | — | — |
| Trimethoprim/ Sulfamethoxazole | ≤0.5/9.5 | ≤0.5/9.5 | — | — |
| Ticarcillin | — | — | 16 | 8~32 |
| Ticarcillin/ Clavulanic acid | — | — | 16/2 | 8/2~32/2 |
| Tobramycin | — | — | 0.25~0.5 | 0.25~1 |
| Time to Result | 3 hr | 16~20 hr | 3 hr | 16~20 hr |

Gram Positive Strains

| | S. aureus ATCC 29213 | | E. faecalis ATCC 27212 | |
|---|---|---|---|---|
| Antimicrobial | SCMA Results | CLSI QC range | SCMA Results | CLSI QC range |
| Ampicillin | 1 | 0.5~2 | 0.5~1 | 0.5~2 |
| Amoxicillin/ Clavulanic acid | 0.25/0.12~ 0.5/0.25 | 0.12/0.06~ 0.5/0.25 | — | — |
| Ciprofloxacin | 0.5 | 0.12~0.5 | 0.5~2 | 0.25~2 |
| Clindamycin | 0.12 | 0.06~0.25 | — | — |
| Erythromycin | 0.25 | 0.25~1 | 1(6 hr) | 1~4 |
| Gentamicin | 0.25~0.5 | 0.12~1 | ≤500 | ≤500 |
| Imipenem | 0.03 | 0.015~0.06 | — | — |
| Levofloxacin | 0.12~0.25 | 0.06~0.3 | 1 | 0.25~2 |
| Linezolid | 1~4 | 1~4 | 1~2 | 1~4 |
| Oxacillin | 0.5 | 0.12~0.5 | — | — |
| Norfloxacin | — | — | 2~4 | 2~8 |
| Penicillin | 0.5 | 0.25~2 | 1~2 | 1~4 |
| Rifampin | 0.004~0.008 (6 hr) | 0.004~0.015 | 0.5 | 0.5~4 |
| Streptomycin High Level | — | — | ≤500 | ≤500 |
| Teicoplantin | — | — | 0.5 | 0.25~1 |
| Tetracycline | 0.12~0.5 | 0.12~1 | 8(6 hr) | 8~32 |
| Trimethoprim/ Sulfamethoxazole | ≤0.5/9.5 | ≤0.5/9.5 | — | — |
| Vancomycin | 1 | 0.5~2 | 2~4 | 1~4 |
| Time to Result | 4 hr | 16~20 hr | 4 hr | 16~20 hr |

Table 5 shows that MIC values obtained by the method according to the inventive concept (i.e., based on an analysis of changes in morphology and growth pattern of a microbial cell) were included within the MIC QC range in accordance with CLSI guidelines. In addition, it generally takes 16-20 hours to obtain the MIC results in accordance with CLSI guidelines, whereas it takes about 3-4 hours to obtain the MIC results using the method according to the inventive concept. That is, it was found that by using the AST method according to the inventive concept, it was possible to rapidly provide accurate data, compared with the conventional AST method in accordance with CLSI guidelines.

[Third Embodiment] AST Method Using an Automated Cell Image Analysis System

An automated image analysis program was coded with MATLAB R2013a (MathWorks). A raw image of RGB format was processed to remove noises therefrom and obtain an image of binary format showing features and background of bacteria. Pixel information associated with the features of bacteria in the image was calculated to obtain information on the region, number and length of bacterial cells. The results are shown in FIG. 7.

[Fourth Embodiment] Comparison of MIC Values According to the Proposed AST Method and the Standard Method (1) Objective Strain 189 strains, which had been isolated from various clinical specimens of patients at Seoul National University Hospital, Korea (SNUH, 149 strains) and Incheon St. Mary's Hospital (ISMH, 40 strains) (42 E. coli, 34 P. aeruginosa, 30 K. pneumoniae, 45 S. aureus, and 38 Enterococcus spp.) were used as the objective strain.

(2) Method of Experiment

The isolated clinical strains were grown in a sheep blood agar medium or a Mueller Hinton Agar (MHA) medium. Before the experiment, each of the strains was subcultured in a cation-adjusted MHB (CAMHB) medium for 20-24 hours. Thereafter, the AST method according to the inventive concept was performed at the same time as the standard BMD method in accordance with CLSI guidelines that was performed as a comparative experiment.

(3) Comparison of MICs and Results

AST results according to the inventive concept were compared with results obtained by the standard BMD method. The results obtained by the comparison were categorized into categorical agreement (CA), minor error (mE), very major error (VME), and major error (ME), in accordance with U.S. Food and Drug Administration Guidance. For example, in the case that the AST results according to the inventive concept coincided with decision by the standard BMD method, the comparison result was defined as categorical agreement (CA). In the case that one of the results obtained by two methods was intermediate and the other was resistant or susceptible, the comparison result was defined as minor error (mE). In the case that the result of the standard BMD method was resistant and the result of the AST method was susceptible, the comparison result was defined as very major error (VME). In the case that the result of the standard BMD method was susceptible and the result of the AST method was resistant, the comparison result was defined as major error (ME). The results are shown in FIG. 8.

Referring to FIG. 8, when the AST according to the inventive concept was used, a rate of CA was 91.5%, and rates of mE, ME, and VME were 6.3%, 2.9%, and 1.4% respectively, and this satisfied the criteria suggested by FDA, which sets the standard for the minimal performance requirements (mE 10%, ME 3.0%, VME 1.5%, CA 90%). Also, low CA was obtained in reactions of gram-negative strains to β-lactam antimicrobial agents, and there were no significant differences between β-lactam and non β-lactam antimicrobial agents.

Accordingly, these results shows that the AST method according to the inventive concept (i.e., based on analysis of changes in morphology and growth pattern of a microbial cell) made it possible to accurately obtain the test results with a faster test time (by about 6-7 times), compared with the standard BMD method in accordance with CLSI guidelines.

[Fifth Embodiment] Evaluation of Error Rate Associated with the Filament and Swelling Formations, in the AST Method According to the Inventive Concept The graph of FIG. 9 shows minor error rate, major error rate, and very major error rate, in the above experiment (i.e., according to the fourth embodiment) for determining susceptibilities of gram-negative strain E. coli, P. aeruginosa, and K. Pneumonia to β-lactam and non-β-lactam antimicrobial agents.

Referring to FIG. 9, in the case of the reaction with β-lactam antimicrobial agents, the major error rate was abruptly decreased (E. coli: from 12.8% to 3.7% and P. aeruginosa: from 48.1% to 9.9%). This means that, for the reaction between the gram-negative strain and the β-lactam antimicrobial agents, the result obtained by the standard BMD method was determined to be resistant. However, when the AST method according to the inventive concept was used, the result was determined to be susceptible for the filament formation, and this made it possible to reduce the major error rate. In addition, it was found that, for the reaction between E. coli and non-β-lactam antimicrobial agents, the use of the AST method according to the inventive concept made it possible to reduce the major error rate.

While the present general inventive concept has been particularly shown and described with reference to exemplary embodiments thereof, it will be understood by those of ordinary skill in the art that various changes in form and details may be made therein without departing from the spirit and scope of the present general inventive concept as defined by the following claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. An antimicrobial susceptibility test (AST) method based on an analysis of changes in morphology and growth pattern of microbial cells under an antimicrobial agent, wherein the AST method comprises the steps of:
   (A) exposing the microbial cells with the antimicrobial agent;
   (B) imaging the microbial cells exposed to the antimicrobial agent in (A) at least twice over time and comparing these images to measure a change in the total length of the cells, a change in the total area of the cells and a change in the total number of cells;
   (C) classifying the change in cellular morphology over time based on the measurement of (B) as follows:
      i) an increase in the total number of cells classifies the change in morphology as dividing;
      ii) an increase in the length of the cells classifies the change in morphology as filament formation;

iii) an increase in the total area of the cells classifies the change in morphology as swelling formation; and
iv) no increase in the total number, the total length, and total area of cells classifies the change in morphology as no change;

(D) determining whether the microbial cells are resistant or susceptible to the antimicrobial agent as follows:
  i) microbial cells classified as dividing in step (C) are resistant to the antimicrobial agent; and
  ii) microbial cells classified as filament formation, swelling formation or no change are susceptible to the antimicrobial agent.

2. The AST method of claim 1, wherein the microbial cells are selected from the group consisting of *Enterococcus faecium, Staphylococcus aureus, Klebsiella species, Acinetobacter baumannii, Pseudomonas aeruginosa*, and *Enterobacter* species.

3. The AST method of claim 1, wherein the antimicrobial agents is at least one selected from the group consisting of Amikacin, Amoxicillin, Ampicillin, Aztreonam, Benzylpenicillin, Clavulanic Acid, Cefazolin, Cefepime, Cefotaxime, Cefotetan, Cefoxitin, Cefpodoxime, Ceftazidime, Ceftriaxone, Cefuroxime, Ciprofloxacin, Dalfopristin, Doripenem, Daptomycin, Ertapenem, Erythromycin, Gentamicin, Imipenem, Levofloxacin, Linezolid, Meropenem, Minocycline, Moxifloxacin, Nitrofurantoin, Norfloxacin, Piperacillin, Quinupristin, Rifampicin, Streptomycin, Sulbactam, Sulfamethoxazole, Telithromycin, Tetracycline, Ticarcillin, Tigecycline, Tobramycin, Trimethoprim, and Vancomycin.

4. The AST method of claim 1, wherein the antimicrobial agent is a beta-lactam antimicrobial agent.

5. The AST method of claim 1, wherein the antimicrobial agent is a penem of a beta-lactam antimicrobial agent.

6. The AST method of claim 5, wherein the microbial cells are gram-negative bacteria, and the antimicrobial agent is imipenem or meropenem.

\* \* \* \* \*